(12) United States Patent
Yamane

(10) Patent No.: US 8,939,900 B2
(45) Date of Patent: Jan. 27, 2015

(54) STOPPER AND ENDOSCOPE

(75) Inventor: Kenji Yamane, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 50 days.

(21) Appl. No.: 13/426,120

(22) Filed: Mar. 21, 2012

(65) Prior Publication Data

US 2012/0253126 A1   Oct. 4, 2012

(30) Foreign Application Priority Data

Mar. 28, 2011 (JP) ................................ P2011-070197

(51) Int. Cl.
  *A61B 1/00* (2006.01)
  *A61B 1/018* (2006.01)
  *A61B 1/04* (2006.01)

(52) U.S. Cl.
  CPC ............. *A61B 1/018* (2013.01); *A61B 1/00137* (2013.01)
  USPC .......................................... 600/154; 600/153

(58) Field of Classification Search
  CPC ........................ A61B 1/00128; A61B 1/00137
  USPC ........ 600/154, 114, 153; 604/167.01–167.06; 403/2; 348/45
  See application file for complete search history.

(56) References Cited

U.S. PATENT DOCUMENTS 5,147,305 A * 9/1992 Nakamura et al. ............ 604/110

FOREIGN PATENT DOCUMENTS

| JP | 2-283345 A | 11/1990 |
|---|---|---|
| JP | 3-042275 A | 2/1991 |
| JP | 2006-055446 A | 3/2006 |
| JP | 2006055446 A * | 3/2006 |
| JP | 2008-043774 A | 2/2008 |
| JP | 2008278906 A * | 11/2008 |

* cited by examiner

Primary Examiner — Alireza Nia
Assistant Examiner — Timothy J Neal
(74) Attorney, Agent, or Firm — Birch, Stewart, Kolasch & Birch, LLP

(57) ABSTRACT

A flange is formed in a ferrule. A forceps stopper has a fixing member engaging with the flange and a stopper body that holds the fixing member. The fixing member has detachable first and second pieces. The stopper body has a fixing member accommodation hole that accommodates the fixing member in a combined state. The stopper body has a fixing member holding portion that holds the fixing member that is accommodated in the fixing member accommodation hole. The fixing member holding portion has an annular contact portion that comes into contact with the fixing member and a connection portion that connects the outer periphery of the annular contact portion to the opening peripheral edge portion of the fixing member accommodation hole. When the stopper body is pulled, the connection portion is broken, so that the holding of the fixing member using the fixing member holding portion is released.

20 Claims, 14 Drawing Sheets

STOPPER AND ENDOSCOPE

BACKGROUND OF THE INVENTION

1. Field of the Invention

The present invention relates to a nonreusable endoscope stopper which is attached to an opening portion of a channel of an endoscope, and an endoscope with a stopper.

2. Description of the Related Art

Hitherto, in the medical field, by inserting an insertion portion of an endoscope into the body of a patient, not only observation inside the body, but also various treatments with respect to the subject observation portion inside the human body have been performed. Specifically, various treatments such as resection and extraction of a subject observation portion have been performed in a manner such that various treatment tools such as forceps or an incision tool are inserted through a forceps channel inside an insertion portion from a forceps opening ferrule provided in an operating portion of an endoscope and protrude from the front end of the insertion portion.

The forceps opening ferrule is equipped with a forceps stopper through which a treatment tool is inserted when performing a treatment (see JP1991-042275A (JP-H3-042275A) and JP1990-283345A (JP-H2-283345A)). The forceps stopper prevents body fluid, waste, air, and the like inside a body from flowing backward inside the forceps channel due to a change in the internal pressure of the body, and from leaking to the outside from the forceps opening ferrule. Since body fluid or the like adheres to the forceps stopper when the forceps stopper is used, a disposable forceps stopper is generally used so as to be replaced with new one after the every use thereof from the viewpoint of preventing infection.

JP2008-043774A discloses a forceps stopper which is detachable from a forceps ferrule by breaking a part of a stopper. Further, JP2006-055446A discloses a forceps stopper that has a stopper body and an engagement portion engaging with a forceps opening ferrule, wherein a notch is formed therebetween. The forceps stopper cannot be used anymore since a portion between the stopper body and the engagement portion is broken when the stopper body is pulled. In the forceps stopper disclosed in JP2008-043774A and JP2006-055446A, the forceps stopper cannot be reused since the forceps stopper is broken when it is detached from the forceps opening ferrule. As a result, it is possible to prevent the used forceps stopper from being reused accidentally.

SUMMARY OF THE INVENTION

In the forceps stopper disclosed in JP2008-043774A, when detaching the forceps stopper from the forceps opening ferrule, it is necessary to perform both an operation of breaking a part of the forceps stopper and an operation of detaching the forceps stopper. For this reason, a problem arises in that it is troublesome to detach the forceps stopper. Further, in the forceps stopper disclosed in JP2006-055446A, the stopper body may be detached by the pulling operation, but the forceps ferrule remains in the engagement portion. Accordingly, it is necessary to additionally perform an operation of detaching the engagement portion by releasing the engagement between the engagement portion and the forceps opening ferrule. For this reason, since the engagement portion may not be simply detached from the forceps opening ferrule, a problem arises in that it is troublesome to detach the forceps stopper as in JP2008-043774A.

The present invention has been made in view of the above-mentioned problems and an object of the present invention is to provide a stopper which is simply detached from an opening portion such as a forceps opening ferrule, and to provide an endoscope which has the stopper.

In order to achieve the above-described object, there is provided a stopper that is installed in an outer surface of an endoscope and is attached to a cylindrical opening portion communicating with a channel inside the endoscope, the stopper including: a cylindrical fixing member that has an insertion hole allowing the opening portion to be inserted thereinto and an engagement portion formed in an inner wall continuous to the insertion hole and engaging with an outer peripheral surface of the opening portion and is divided into plural pieces along the circumferential direction of the insertion hole; a stopper body that has an accommodation hole accommodating the fixing member in a combined state and is attached to the opening portion through the fixing member; and a fixing member holding portion that is installed in the stopper body, holds the fixing member with accommodation in the accommodation hole, and is broken so as to release the holding of the fixing member when the stopper body is pulled toward the front side of the opening portion. Furthermore, the cylindrical shape indicates a hollow cylindrical shape, and the cross-section perpendicular to the axial direction is, for example, a circular shape, an oval shape, and a polygonal shape.

The engagement portion may be an annular protrusion that is formed in an inner surface of the insertion hole along the circumferential direction of the insertion hole and is divided into a plurality of pieces along the circumferential direction, and the annular protrusion may engage with a flange that is formed in the outer peripheral surface of the opening portion.

The inner diameter of the annular protrusion may be equal to or larger than the outer diameter of the opening portion and be smaller than the outer diameter of the flange.

The fixing member holding portion may have an annular contact portion that is formed on an opening of the accommodation hole and comes into contact with the annular protrusion and a connection portion that connects an opening peripheral edge portion of the accommodation hole to the contact portion at a plurality of positions. When the stopper body is pulled, the connection portion may be broken.

The stopper body may be formed of an elastic material. The accommodation hole may be deformed so as to increase in diameter in a manner such that the annular protrusion is widened in the radial direction by the flange until the annular protrusion comes into contact with the flange and rides over the flange when the opening portion is inserted into the insertion hole, and restore to an original shape when the annular protrusion rides over the flange.

The annular protrusion may have an inclined surface that is formed by cutting an opening peripheral edge portion on the opposite side of a forward direction. Further, the fixing member may be formed of a rigid material. Further, the fixing member may be divided into two pieces along the circumferential direction of the opening portion.

Further, an endoscope has: an operating portion that is connected to a base end portion of an insertion portion inserted into a subject; a cylindrical opening portion that is formed in an outer peripheral surface of the operating portion and communicates with a channel inserted through the insertion portion; and the stopper that is attached to the opening portion described above.

The channel may be a treatment tool channel through which a treatment tool is inserted.

In the stopper and the endoscope of the present invention, the fixing member which engages with the outer peripheral surface of the opening portion has a divided structure, and the fixing member holding portion which holds the fixing member inside the stopper body in a combined state is broken so as to release the holding of the fixing member when the stopper body is pulled, so that the fixing member is divided so as to be simply detached from the opening portion. As a result, since there is no need to perform an operation of breaking a part of the stopper or releasing the engagement with the opening portion in addition to the pulling operation, the stopper may be simply detached from the opening portion compared to the related art. Further, since the fixing member holding portion is broken, the fixing member may not be held inside the stopper body again. As a result, since the fixing member may not engage with the outer peripheral surface of the ferrule, the stopper may be prevented from being reused.

DESCRIPTION OF THE PREFERRED EMBODIMENTS

Figure 1:
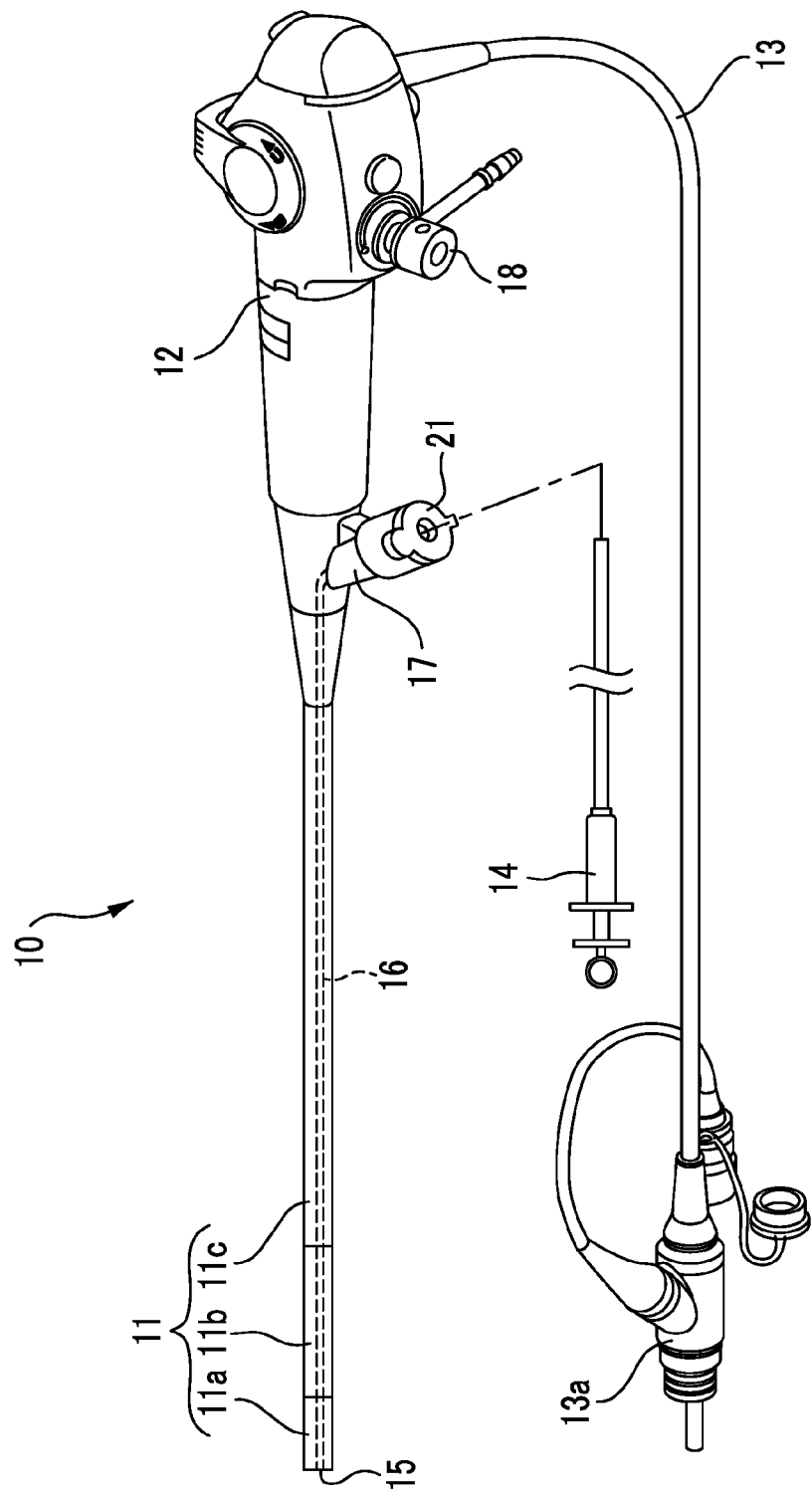
FIG. 1 is a perspective view illustrating an endoscope.

As shown in FIG. 1, an endoscope 10 is, for example, a bronchoscope which is inserted into a trachea, and has an insertion portion 11 which is inserted into the trachea, an operating portion 12 which extends to the base end portion of the insertion portion 11, and a universal cord 13 which is connected to the operating portion 12. The universal cord 13 is connected to a processor device or a light source device (not shown) through a complex type connector 13a.

The insertion portion 11 has the following portions from the front end side toward the base end side, that is, a front-end rigid portion 11a, a curved portion 11b which is able to be curved, and a flexible tube portion 11c. The front end surface of the front-end rigid portion 11a is provided with an observation window or an illumination window (not shown) in addition to a forceps outlet 15 which is an outlet of a treatment tool 14 such as forceps. An image sensor (not shown) is disposed on the inside of the observation window, and an optical fiber cable (not shown) is disposed on the inside of the illumination window. The signal line of the image sensor and the optical fiber cable are respectively connected to the processor device and the light source device through the insertion portion 11, the universal cord 13, and the connector 13a.

A forceps channel (a treatment tool channel) 16 through which the treatment tool 14 is inserted is disposed inside the insertion portion 11. One end of the forceps channel 16 is connected to the forceps outlet 15, and the other end thereof is connected to a forceps opening 17 which is provided in the operating portion 12. Further, the forceps channel 16 is also used as a path which suctions a body fluid such as blood or solid matter such as body waste matter from the forceps outlet 15. A suction channel (not shown) which is branched from the forceps channel 16 is disposed inside the operating portion 12, and the suction path is connected to a suction button 18 which is installed in the operating portion 12.

A negative pressure source (not shown) is connected to the suction button 18 in addition to the operating portion 12. The suction button 18 switches the communication state and the interruption state between the suction path and the negative pressure source by the pressing operation or the press releasing operation.

Figure 2:
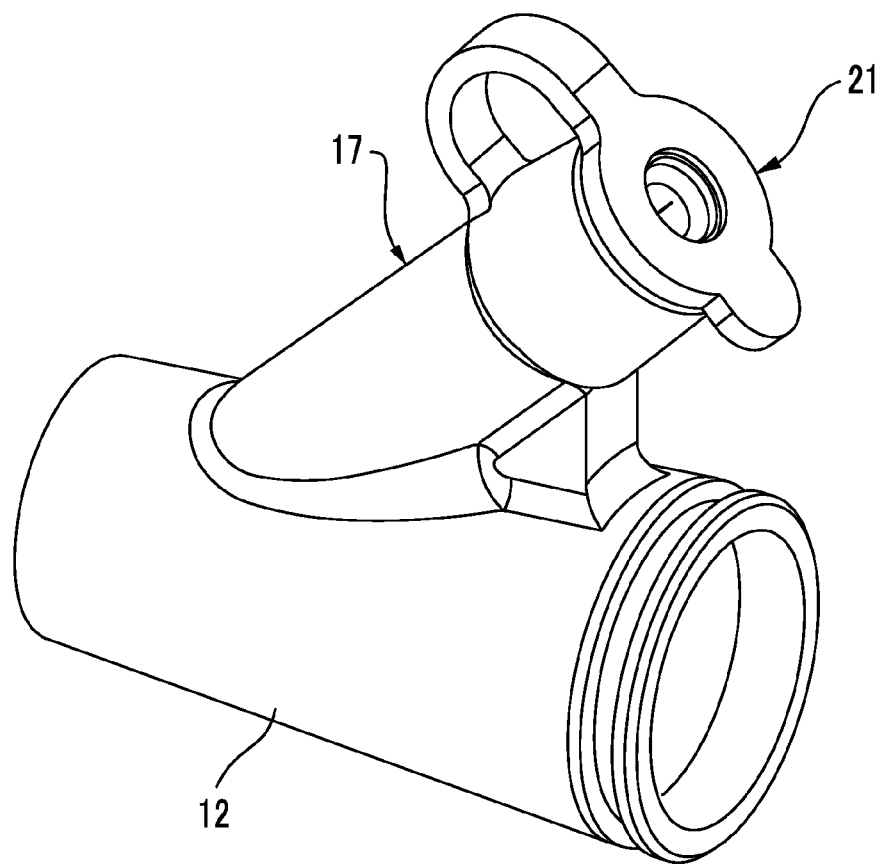
FIG. 2 is a perspective view illustrating a forceps opening and a forceps stopper.

As shown in FIG. 2, the forceps opening 17 is equipped with a disposable forceps stopper (a stopper) 21 into which the treatment tool 14 is inserted through a forceps opening ferrule (hereinafter, simply referred to as a ferrule and see FIG. 3) 20 which corresponds to the opening portion of the present invention. The forceps stopper 21 prevents a body fluid, waste matter, air, and the like inside the body from flowing backward inside the forceps channel 16 so as to leak to the outside from the ferrule 20 when a treatment is performed by using the treatment tool 14.

Figure 3:
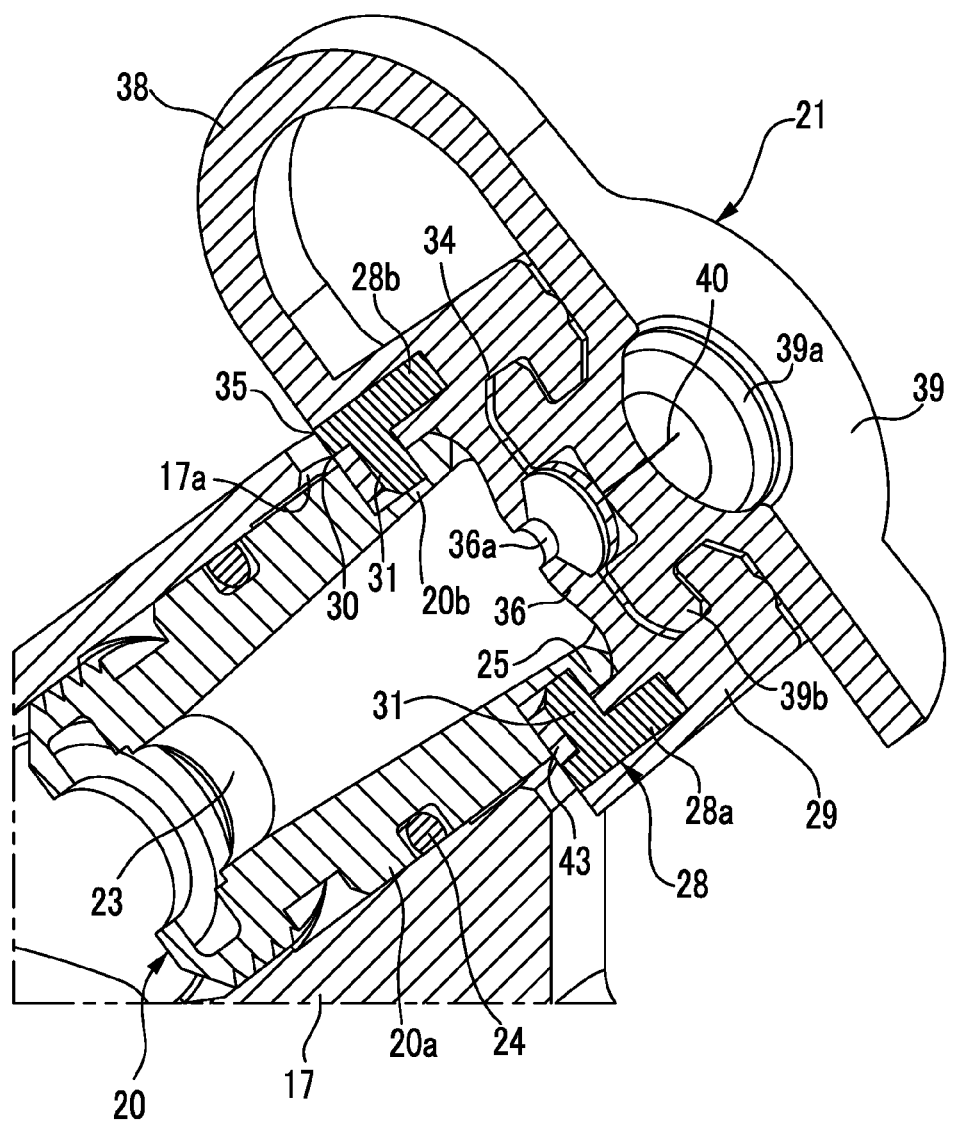
FIG. 3 is a cross-sectional view illustrating a ferrule and a forceps stopper.
Figure 4:
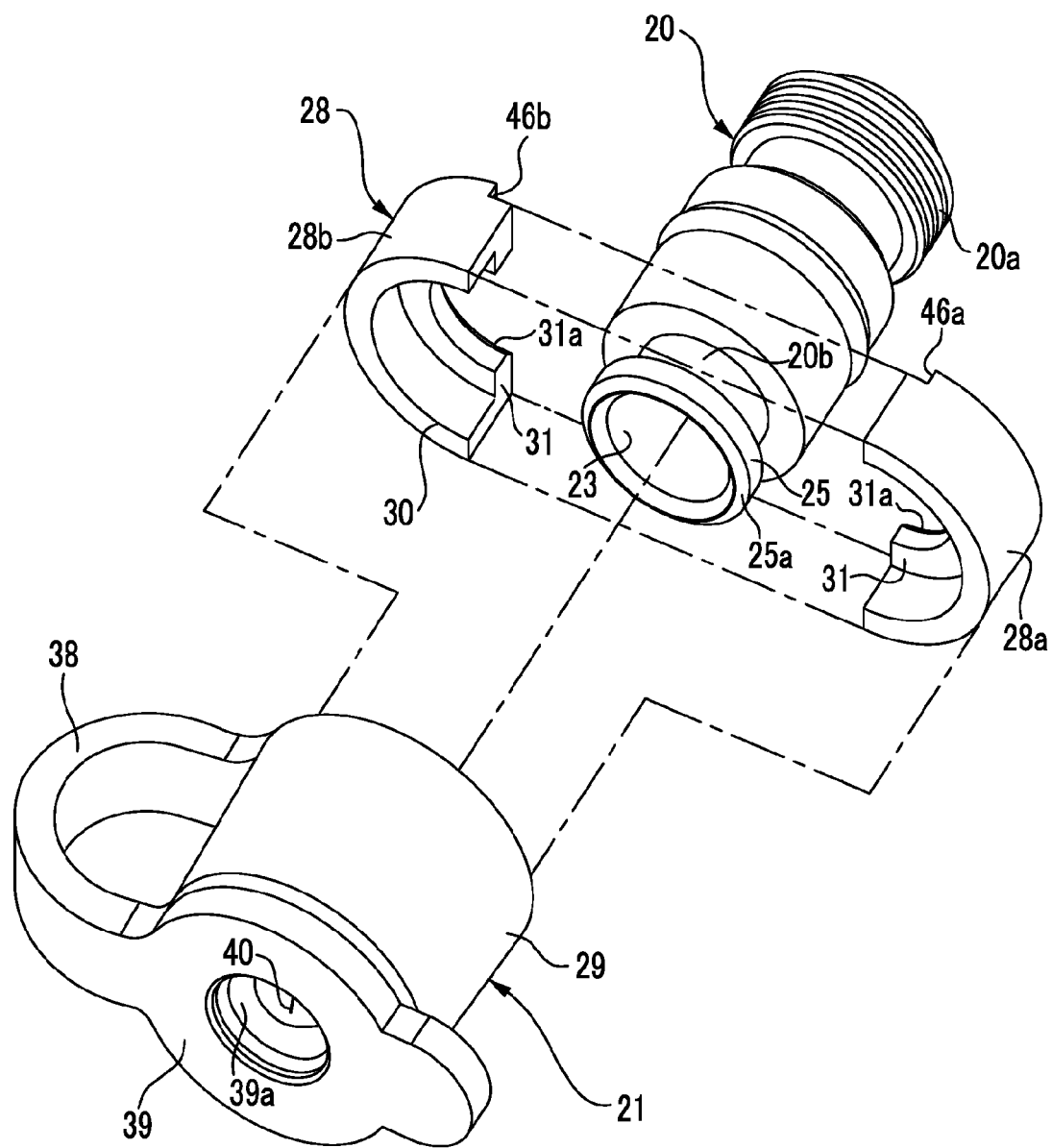
FIG. 4 is an exploded perspective view illustrating a forceps stopper.
Figure 5:
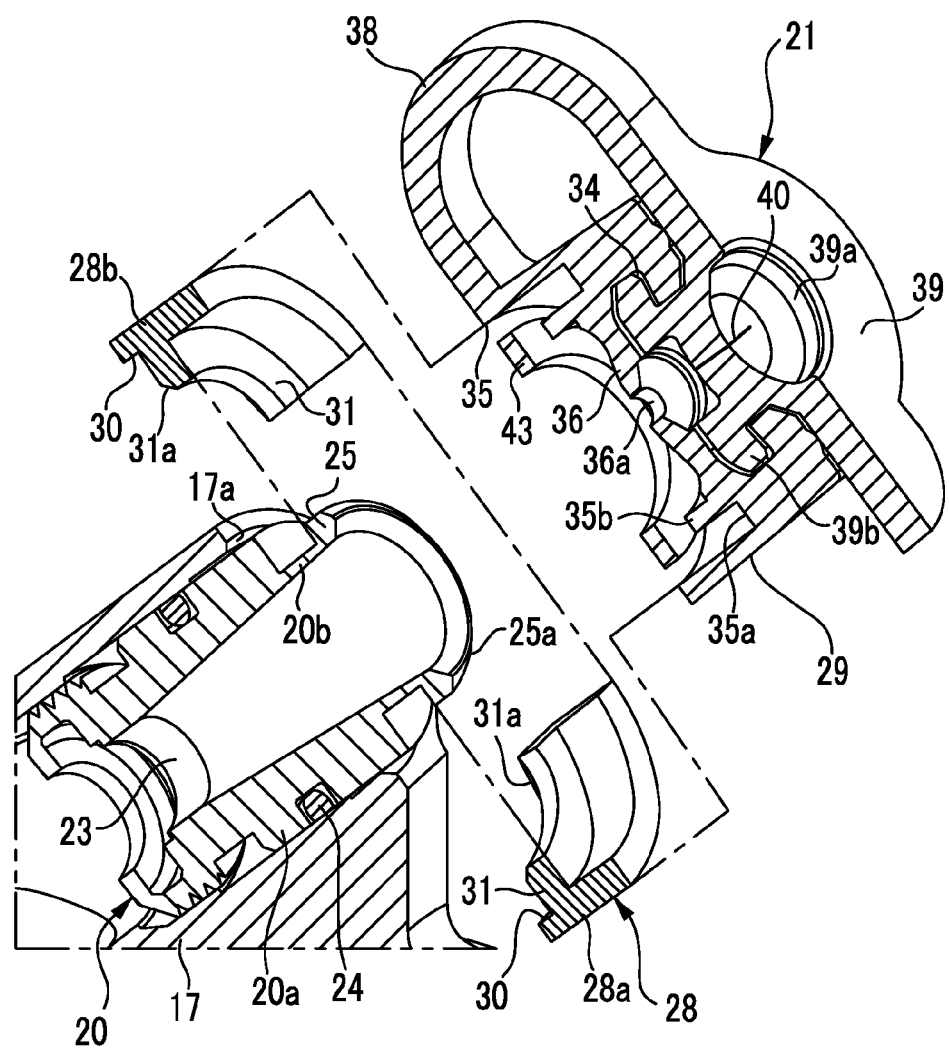
FIG. 5 is a cross-sectional view illustrating the ferrule and the forceps stopper of FIG. 4.

As shown in FIGS. 3 to 5, the ferrule 20 has an inner pipe line 23 which communicates with the forceps channel 16, and is formed by a ferrule body portion 20a which is fixed to the inside of the opening portion 17a of the forceps opening 17 and a front-end ferrule portion 20b which protrudes toward the front side of the opening portion 17a. A packing 24 which prevents the leakage of a body fluid from a gap between the inner peripheral surface of the forceps opening 17 and the outer peripheral surface of the ferrule body portion 20a is fitted to the outer peripheral surface thereof. Hereinafter, the front-side direction of the opening portion 17a is simply referred to as a "forward direction", and the inside direction of the ferrule 20 on the opposite side of the front-side direction is simply referred to as an "inward direction". Further, in the respective portions of the ferrule 20 and the forceps stopper 21, the end portions and the end surfaces in the forward direction are respectively referred to as the forward end portions and the forward end surfaces, and the end portions and the end surfaces in the inward directions are respectively referred to as the inward end portions and the inward end surfaces.

The front-end ferrule portion 20b is formed so that the outer diameter thereof is smaller than the outer diameter of the ferrule body portion 20a. The front end of the front-end ferrule portion 20b is provided with a flange 25 with which the forceps stopper 21 engages. The flange 25 is provided with an inclined surface (hereinafter, simply referred to as a flange inclined surface) 25a which is formed by cutting a corner portion formed between the forward end surface and the outer peripheral surface.

The forceps stopper 21 is formed of a substantially cylindrical rigid fixing member (hereinafter, simply referred to as a fixing member) 28 which is formed of a rigid material such as metal and engages with the flange 25, and a substantially cylindrical stopper body 29 which is formed of an elastic material such as a resin and accommodates the fixing member 28.

The fixing member 28 has an insertion hole 30 into which the front-end ferrule portion 20b is inserted. The fixing member 28 is divided into two pieces, that is, first and second pieces 28a and 28b which are formed in a substantially semicircular cylindrical shape along the circumferential direction of the front-end ferrule portion 20b (hereinafter, simply referred to as a ferrule circumferential direction).

Further, the fixing member 28 is provided with an annular protrusion 31 which engages with the flange 25 along the circumferential direction of the inner wall continuous to the insertion hole 30. The inner diameter of the annular protrusion 31 is equal to or larger than the outer diameter of the front-end ferrule portion 20b and is smaller than the outer diameter of the flange 25. Further, the annular protrusion 31 is divided into two pieces so as to correspond to two divided pieces of the fixing member 28.

Furthermore, the annular protrusion 31 is provided with an inclined surface (hereinafter, simply referred to as a protrusion inclined surface) 31a which is formed by cutting the opening peripheral edge portion of the insertion hole 30 in the inward direction. The protrusion inclined surface 31a is inclined in the direction opposite to the flange inclined surface 25a.

The stopper body 29 has a cap attachment hole 34 which is opened to the forward end portion and a fixing member accommodation hole 35 which is opened to the inward end portion. The cap attachment hole 34 and the fixing member accommodation hole 35 are divided by a partition wall 36 which is provided inside the stopper body 29. The partition wall 36 is provided with a small hole 36a into which the treatment tool 14 is inserted. The small hole 36a is formed so as to be smaller than the outer diameter of the treatment tool 14.

Further, the stopper body 29 is integrally provided with a cap 39 through a connection belt 38. A concave portion 39a which serves as the inlet of the treatment tool 14 is formed in the forward end surface of the cap 39, and a downward convex fitting portion 39b which is fitted to the cap attachment hole 34 is formed in the inward end surface. The bottom surface of the concave portion 39a is provided with a slit 40 which reaches the front end of the fitting portion 39b.

The slit 40 maintains a water-tight state and an air-tight state by the elasticity of the cap 39 in a state where the treatment tool 14 is not inserted. Further, in a state where the treatment tool 14 is inserted, the slit 40 prevents a body fluid from flowing backward so as to leak therefrom in a manner such that the inner peripheral surface of the slit comes into close contact with the outer peripheral surface of the treatment tool 14 due to the elasticity of the cap 39.

The fixing member accommodation hole 35 accommodates the fixing member 28. At this time, since the inner wall surface of the fixing member accommodation hole 35 comes into contact with the outer peripheral surface of the fixing member 28, the combined state between the first piece 28a and the second piece 28b is maintained. Further, the bottom surface of the fixing member accommodation hole 35 is formed so as to enclose the inward end surface of the partition wall 36 and the partition wall 36, and is formed by a bottom surface of a fitting groove 35a (see FIG. 5) to which the forward end portion of the fixing member 28 is fitted.

A cylindrical receiving portion 35b (see FIG. 5) which comes into contact with the base portion of the annular protrusion 31 is formed between the partition wall 36 and the fitting groove 35a. Further, the front-end ferrule portion 20b and the flange 25 are fitted to the concave portion which is formed by the inner surface of the receiving portion 35b and the partition wall 36 when the forceps stopper 21 is attached to the ferrule 20. Accordingly, the inner pipe line 23, the small hole 36a and the slit 40 are disposed so as to be coaxial. For this reason, the treatment tool 14 is inserted into the forceps channel 16 through the slit 40, the small hole 36a, and the inner pipe line 23.

Figure 6:
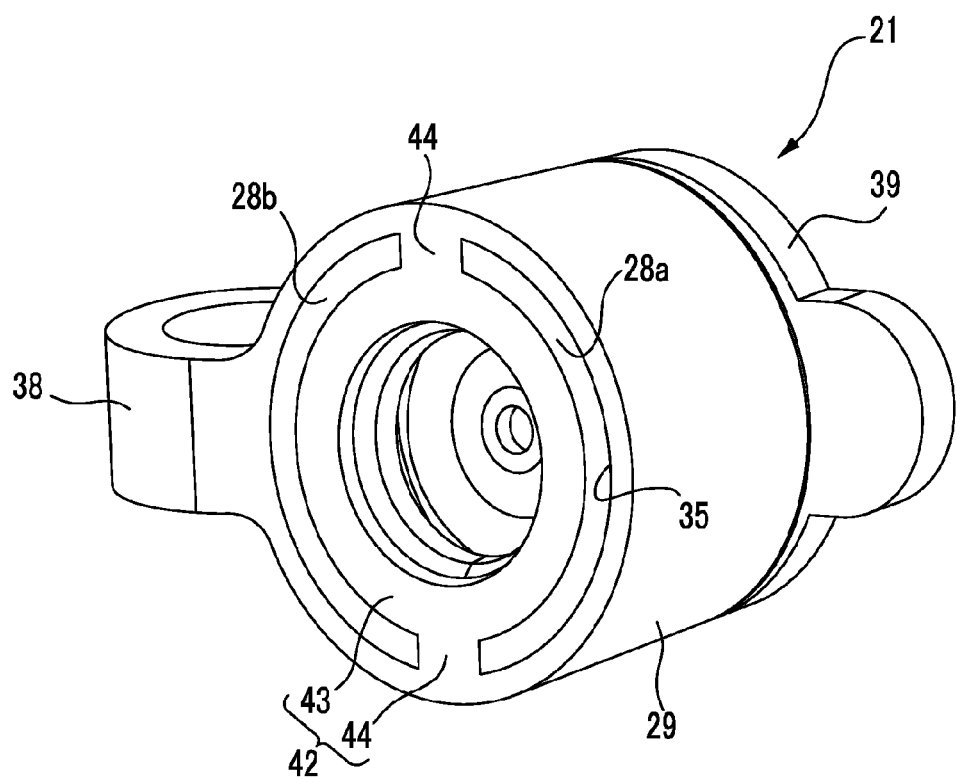
FIG. 6 is a perspective view illustrating the forceps stopper when seen from the bottom surface side thereof.

As shown in FIG. 6, the stopper body 29 is provided with a fixing member holding portion 42 which accommodates the fixing member 28 in the fixing member accommodation hole 35. The fixing member holding portion 42 includes an annular contact portion (hereinafter, simply referred to as an annular contact portion) 43 which is formed on the opening of the fixing member accommodation hole 35 and comes into contact with the inward end surface of the annular protrusion 31, and a connection portion 44 which connects the outer periphery of the annular contact portion 43 to the opening peripheral edge portion of the fixing member accommodation hole 35 at two positions.

The width or the thickness of the connection portion 44 is adjusted so that the connection portion is broken when a predetermined force or greater is applied thereto. Accordingly, the fixing member holding portion 42 holds the fixing member 28 in the fixing member accommodation hole 35 until the connection portion 44 is broken. Then, when the connection portion 44 is broken, a part of the fixing member 28 is no longer accommodated in the fixing member accommodation hole 35, so that the holding of the fixing member 28 is released.

Next, the operation of the forceps stopper 21 with the above-described configuration, and particularly, the process in which the forceps stopper 21 is attached to and detached from the ferrule 20 will be described.

[Forceps Stopper Attachment Process]

Figure 7:
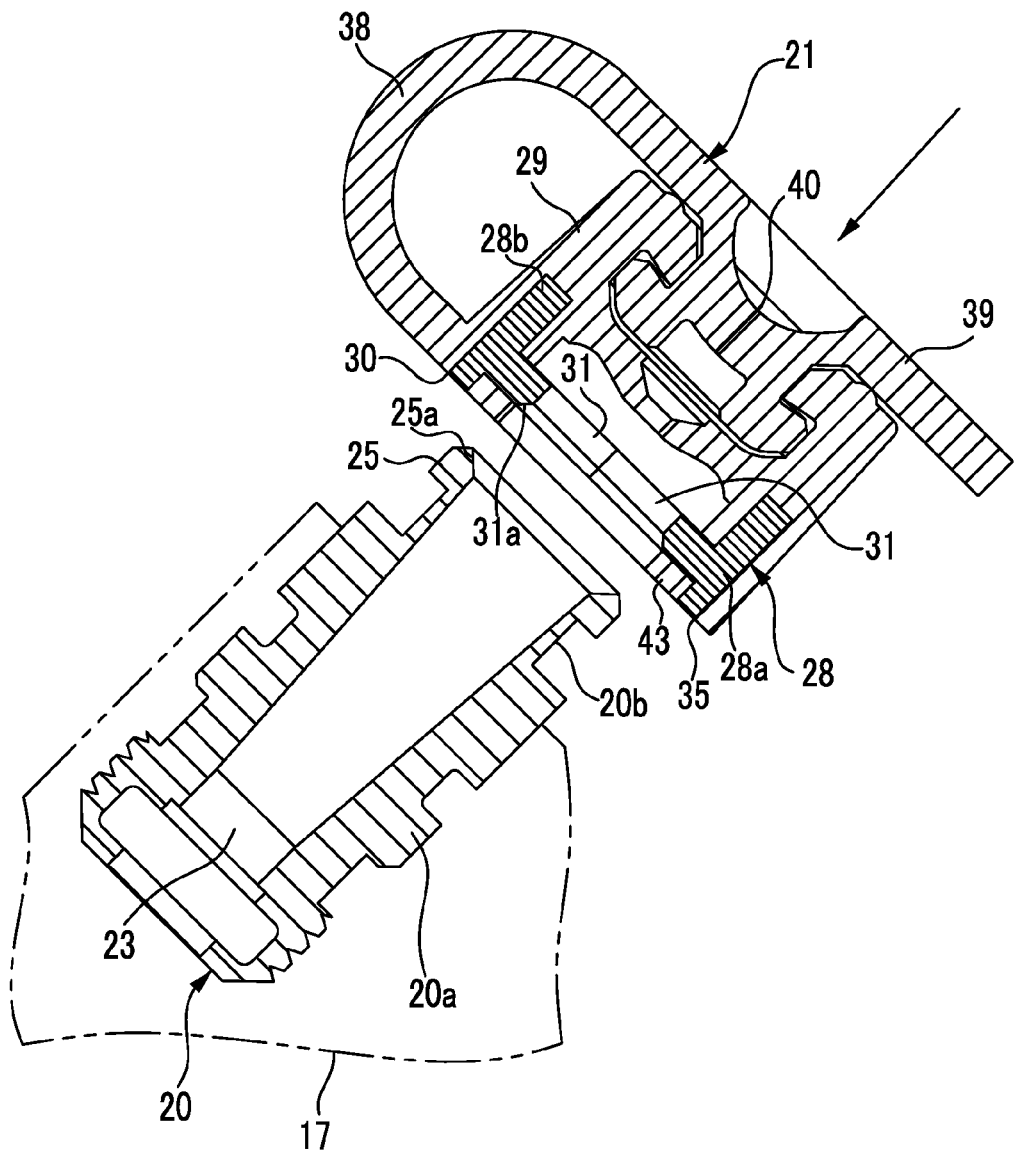
FIG. 7 is a diagram illustrating a state where the forceps stopper is not attached yet.

As shown in FIG. 7, first, the position of the forceps stopper 21 is adjusted so that the center of each of the annular contact portion 43, the insertion hole 30, and the fixing member accommodation hole 35 matches the center of the front-end ferrule portion 20b. Subsequently, the forceps stopper 21 is pressed toward the front-end ferrule portion 20b Accordingly, the front-end ferrule portion 20b and the flange 25 (hereinafter, simply referred to as the flange 25 and the like) are inserted into the opening of the annular contact portion 43.

The annular contact portion 43 is gradually deformed so as to increase in diameter with the inserting of the flange 25 and the like in a manner such that the inner periphery thereof is pressed by the flange inclined surface 25a. At this time, since the forward end surface of the annular contact portion 43 comes into contact with the annular protrusion 31, the forward movement of the annular contact portion 43 with the inserting of the flange 25 and the like is regulated by the annular protrusion 31. For this reason, no large force is applied to both connection portions 44, and both connection portions 44 is not broken.

When the flange 25 and the like pass through the opening of the annular contact portion 43, the flange inclined surface 25a comes into contact with the protrusion inclined surface 31a of the annular protrusion 31.

Figure 8:
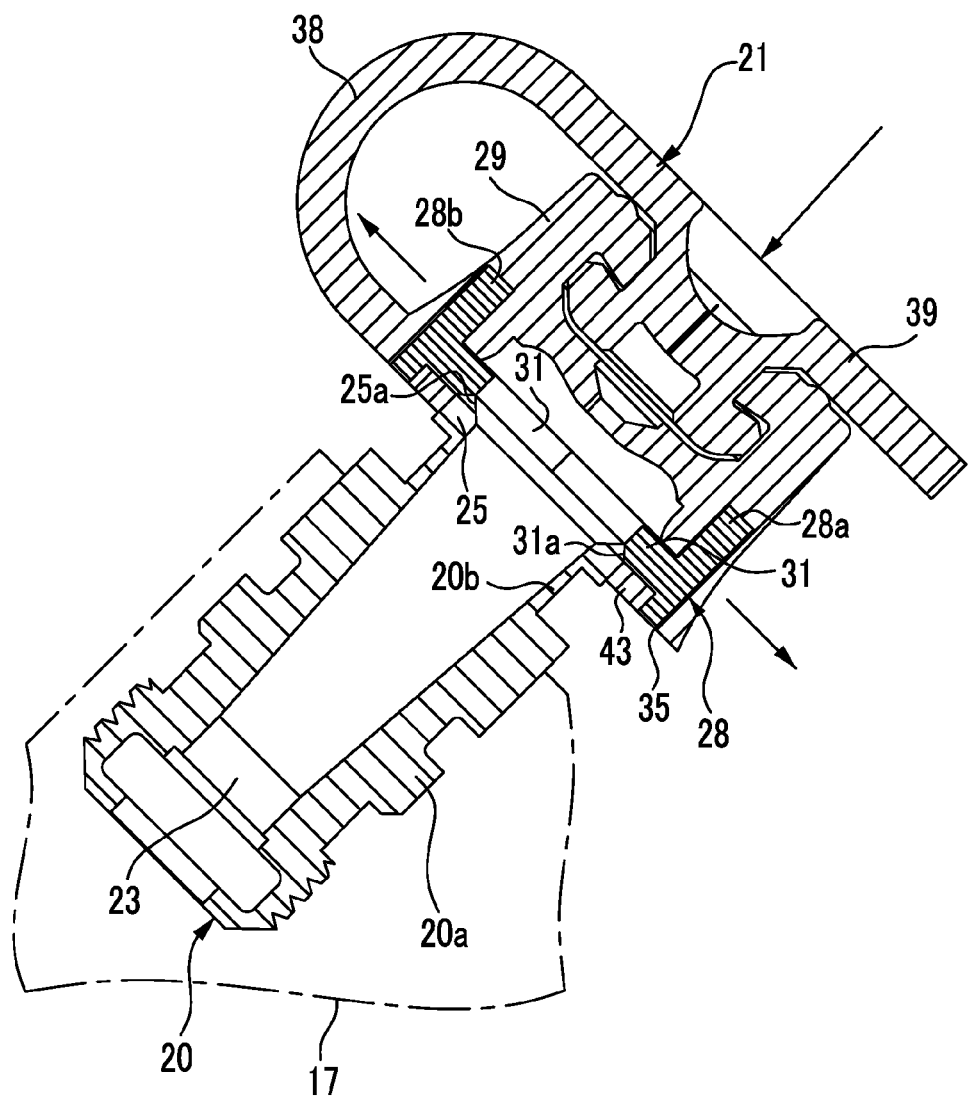
FIG. 8 is a diagram illustrating a state between the time when an annular protrusion comes into contact with a flange to when the ferrule rides over the flange when attaching the forceps stopper.

As shown in FIG. 8, when the pressing operation is continued, the protrusion inclined surface 31a relatively moves inward along the flange inclined surface 25a. Accordingly, the fixing member 28 is divided into the first piece 28a and the second piece 28b, so that the inner diameter gradually increases. Further, the fixing member accommodation hole 35 is also gradually deformed so as to increase in diameter by the inward pressing with an increase in diameter. In this way, when the inner diameters of the first and second pieces 28a and 28b temporarily increase in diameter by elastically deforming the stopper body 29 with the inserting of the flange 25 and the like, the annular protrusion 31 may ride over the flange 25.

Figure 9:
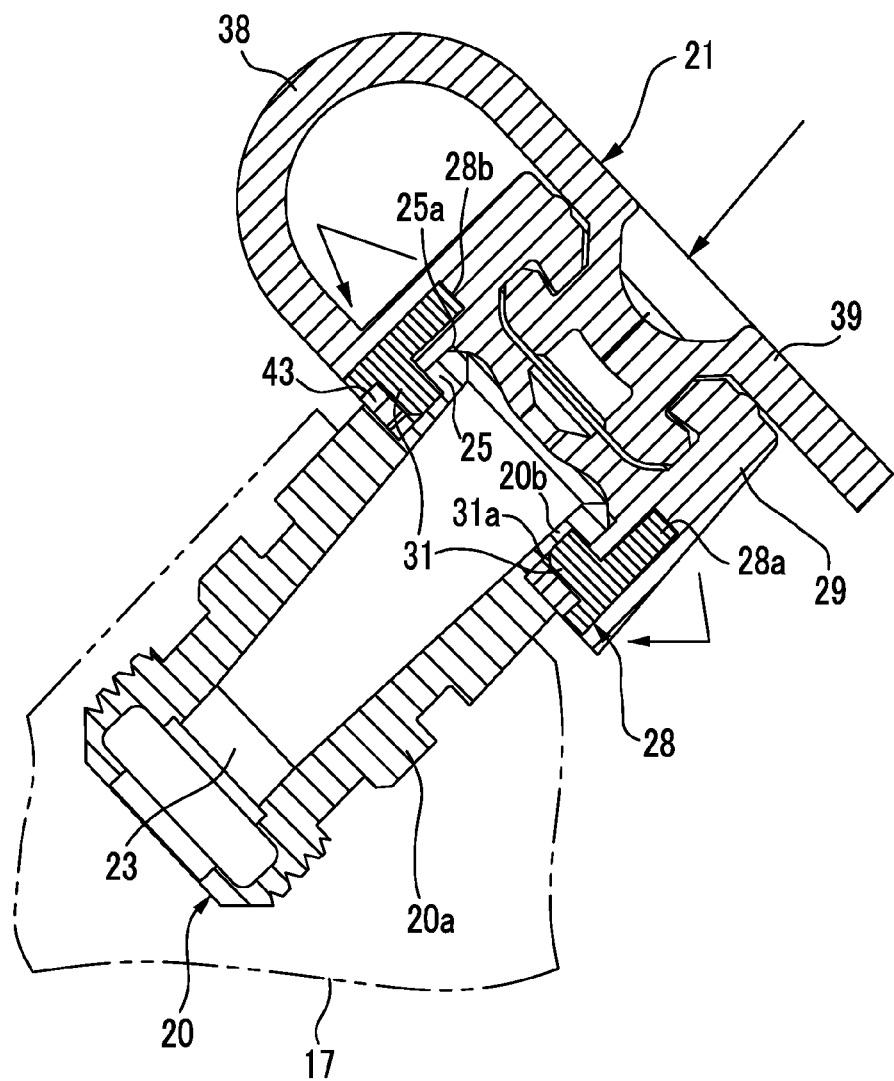
FIG. 9 is a diagram illustrating a state after the annular protrusion of the forceps stopper rides over the flange of the ferrule.

As shown in FIG. 9, when the annular protrusion 31 rides over the flange 25, the fixing member accommodation hole 35 restores to an original shape. Accordingly, the first and second pieces 28a and 28b are combined with each other so as to become the fixing member 28, and the annular protrusion 31 engages with the flange 25. With the above-described operation, the attachment of the forceps stopper 21 is completed. Then, the treatment tool 14 is inserted from the forceps stopper 21 into the forceps channel 16 so as to perform various treatments, and then a process of detaching the forceps stopper 21 starts.

[Forceps Stopper Detaching Process]

Figure 10:
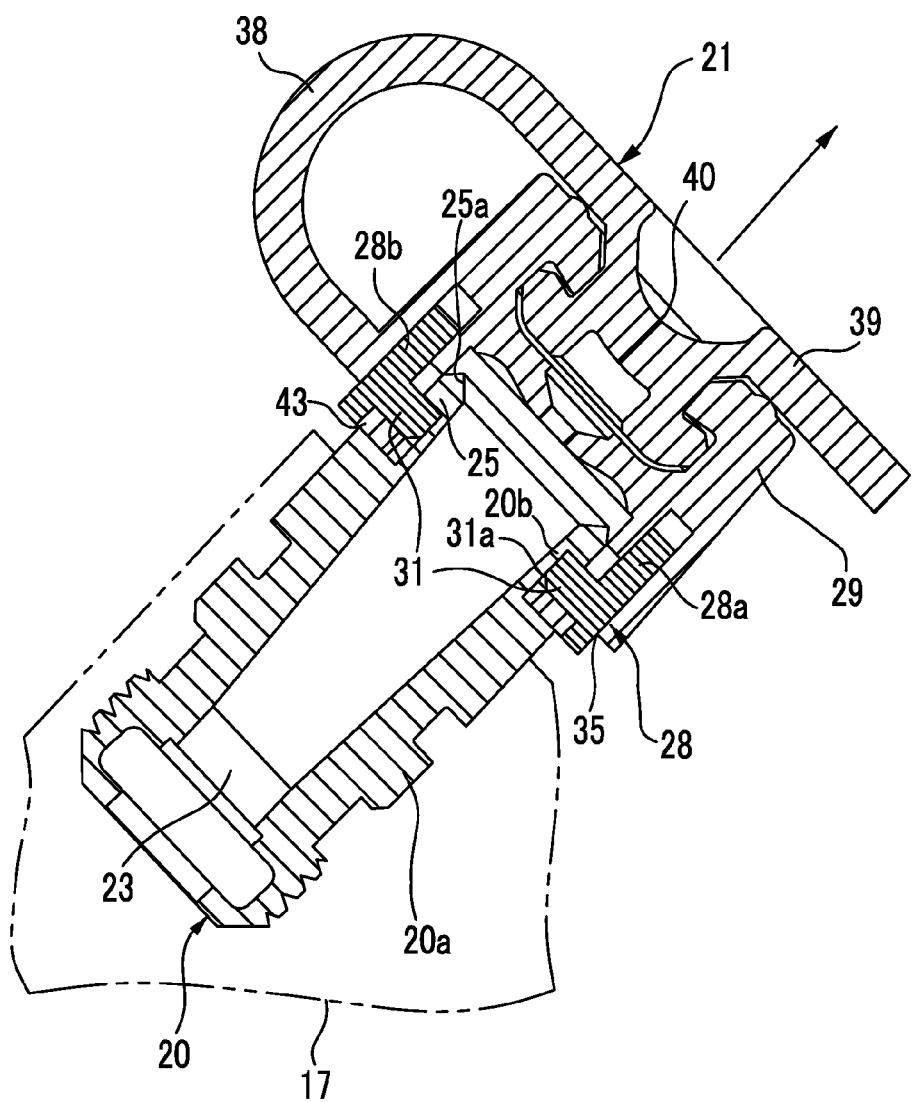
FIG. 10 is a diagram illustrating a state where an operation of pulling a stopper body starts in order to detach the forceps stopper from the ferrule.

As shown in FIG. 10, when the forceps stopper 21 is detached from the ferrule 20, the stopper body 29 is pulled forward. Accordingly, the stopper body 29 moves forward. On the contrary, the fixing member 28 is fixed to the front-end ferrule portion 20b because the annular protrusion 31 engages with the flange 25. For this reason, since the forward movement of the annular contact portion 43 is regulated by the annular protrusion 31, the annular contact portion 43 relatively moves inward with respect to the stopper body 29.

Figure 11:
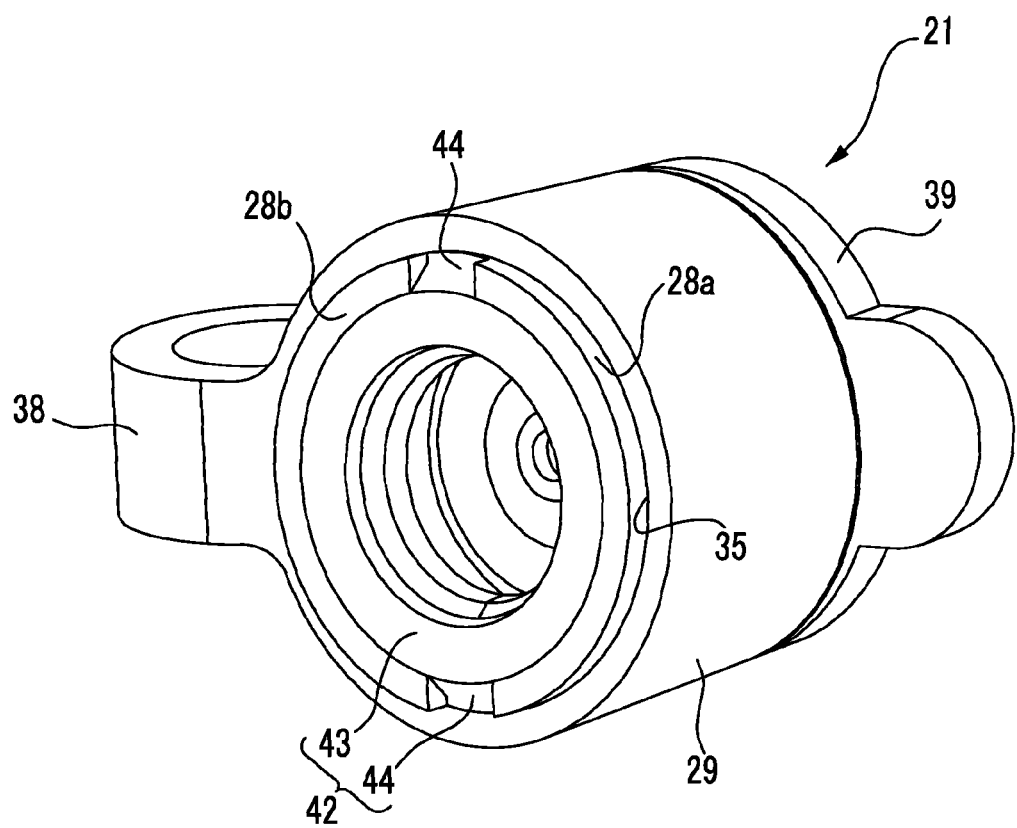
FIG. 11 is a diagram illustrating a state where the connection portion extends by the operation of pulling the stopper body.

As shown in FIG. 11, when the annular contact portion 43 relatively moves inward with respect to the stopper body 29, an inward force is applied to both connection portions 44, so that both connection portions 44 gradually extend. Then, when the pulling operation is continued, the force applied to both connection portions 44 gradually increases, and both connection portions 44 gradually extend.

Figure 12:
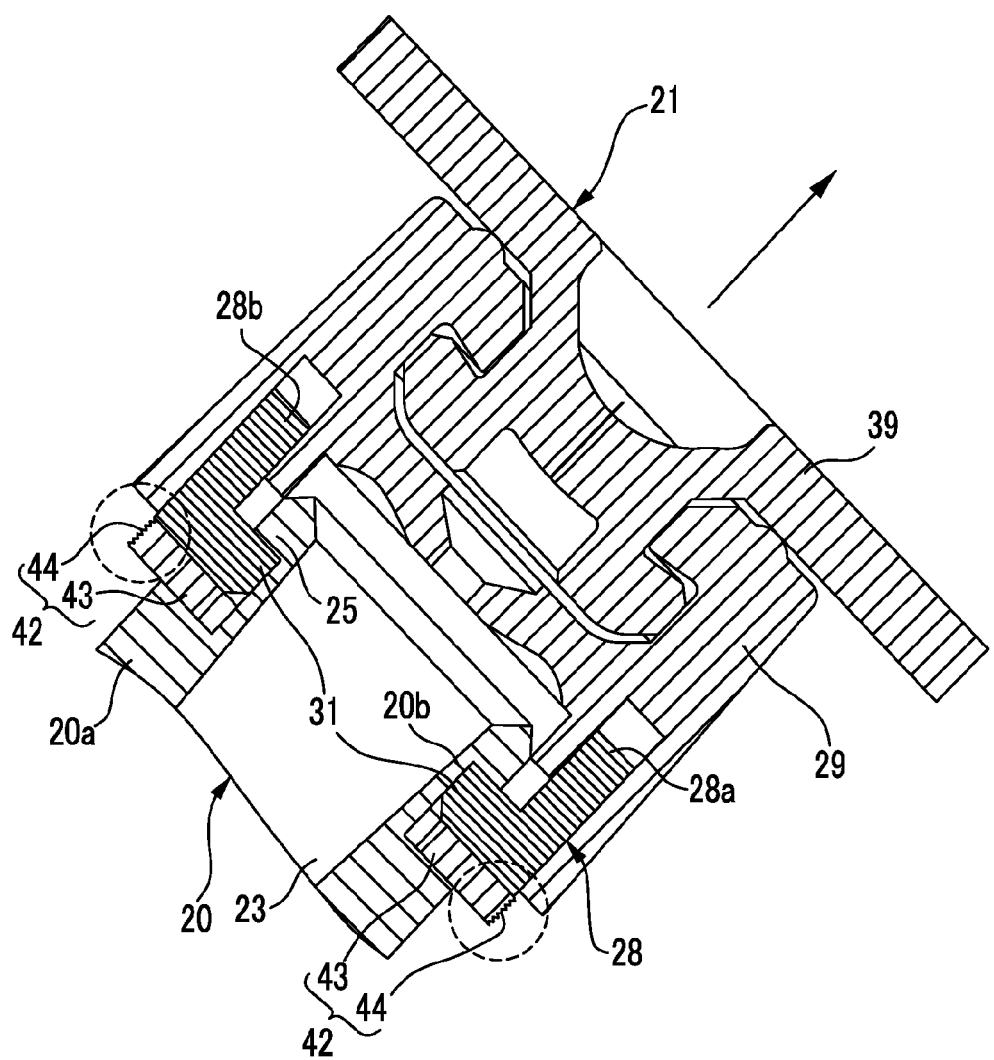
FIG. 12 is a diagram illustrating a state where the connection portion is broken by the operation of continuously pulling the stopper body.

As shown in FIG. 12, when a predetermined force or greater is applied to both connection portions 44, so that the extension of both connection portions 44 exceeds the limit thereof, both connection portions 44 are broken (which is marked as a dotted circle in the drawing). Accordingly, the holding of the fixing member 28 using the stopper body 29 is released. Furthermore, the breakage position of both connection portions 44 is not limited to the portion shown in the drawings, and the breakage occurs in any one of the connection portions 44. Further, only one of two connection portions 44 may be broken.

Figure 13:
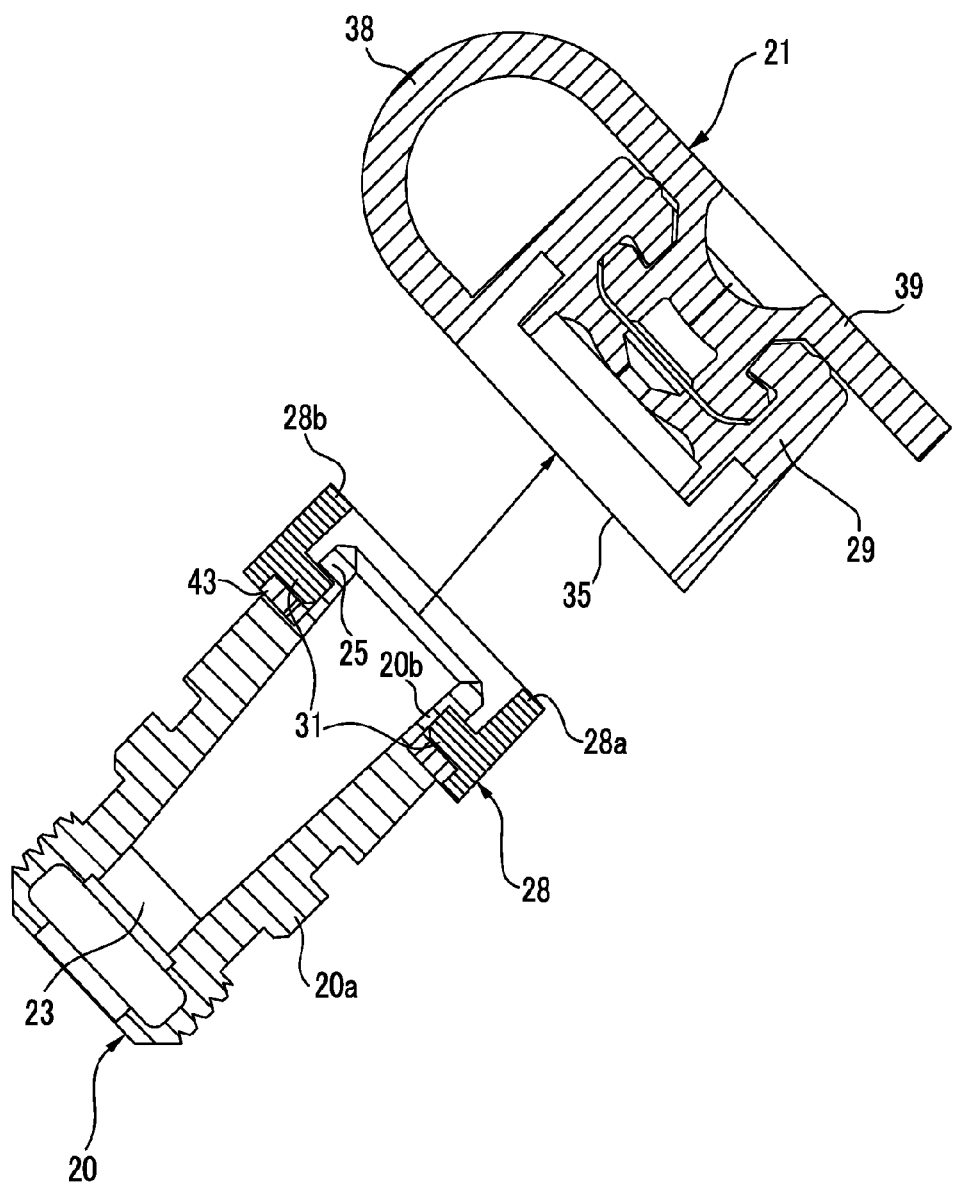
FIG. 13 is a diagram illustrating a state where only the stopper body is detached with the fixing member left in the ferrule due to the breakage of the connection portion.
Figure 14:
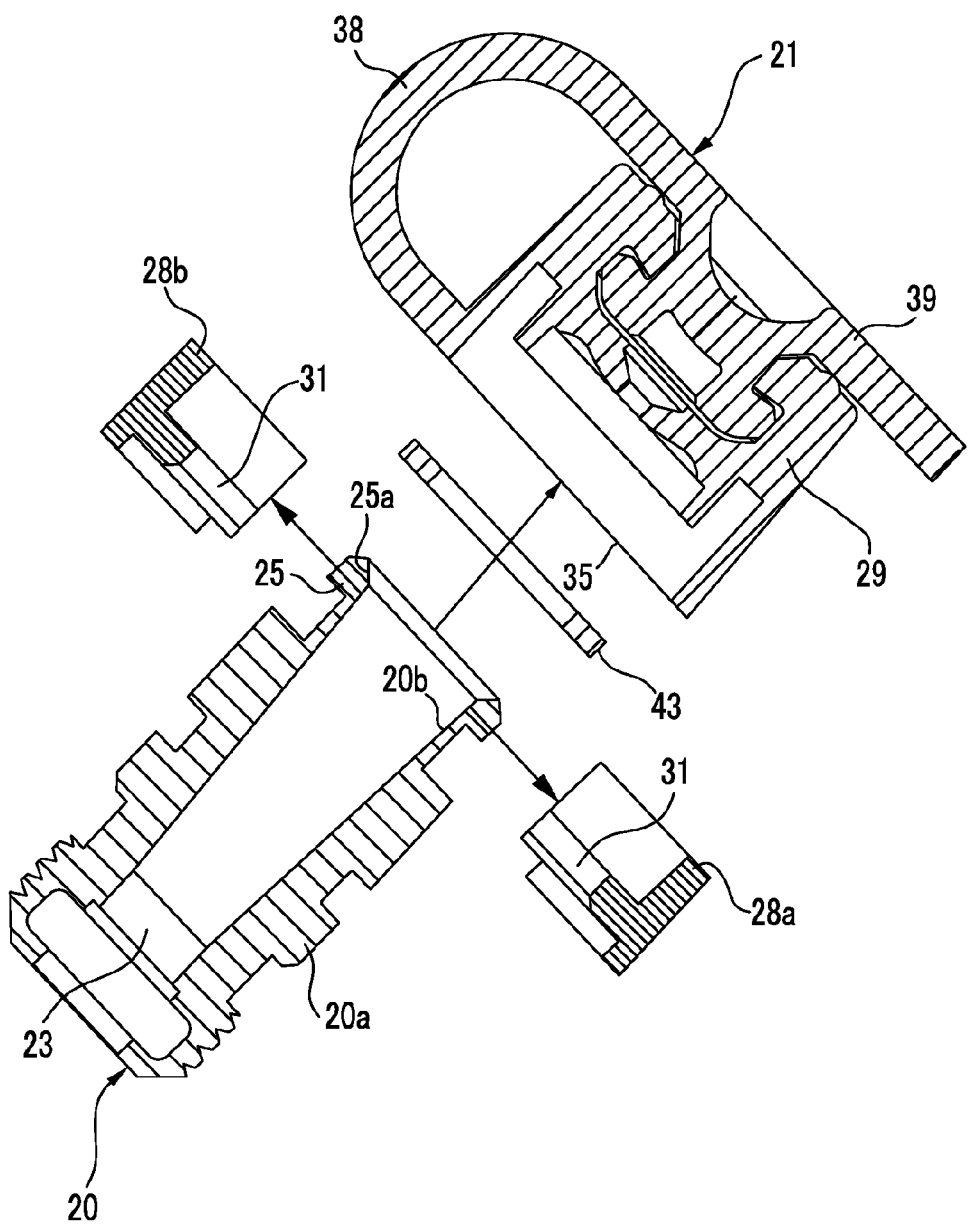
FIG. 14 is a diagram illustrating a state where the fixing member is divided and detached from the ferrule after the stopper body is detached.

As shown in FIG. 13, since both connection portions 44 are broken, only the stopper body 29 is detached from the front-end ferrule portion 20b while the fixing member 28 remains in the front-end ferrule portion 20b. As shown in FIG. 14, since the fixing member 28 is divided into two pieces, the fixing member may be simply detached from the front-end ferrule portion 20b by dividing the fixing member into the first piece 28a and the second piece 28b. Further, since the annular contact portion 43 also does not engage with the front-end ferrule portion 20b or the flange 25, the annular contact portion may be simply detached. With the above-described operation, the process of detaching the forceps stopper 21 is completed.

Since the respective portions of the forceps stopper 21 may be detached from the ferrule 20 by automatically breaking both connection portions 44 with the operation of pulling the stopper body 29, there is no need to perform an operation of breaking a part of the forceps stopper 21 in addition to the pulling operation. Further, a part of the forceps stopper 21 is not maintained so as to engage with the ferrule 20 after the pulling operation. As a result, it is possible to simply detach the forceps stopper 21.

Further, since at least one of both connection portions 44 is broken, the stopper body 29 which is detached from the ferrule 20 may not hold the fixing member 28 inside the fixing member accommodation hole 35 again. For this reason, since the fixing member 28 may not be fixed to the front-end ferrule portion 20b again, the forceps stopper 21 is prevented from being reused.

In the above-described embodiment, the ferrule 20 is provided with the flange 25, and the inner surface of the fixing member 28 is provided with the annular protrusion 31 which engages with the flange 25. However, when the fixing member 28 may engage with the outer peripheral surface of the ferrule 20, the type of the subject engagement portion provided in the ferrule 20 and the type of the engagement portion provided in the inner surface of the fixing member 28 are not particularly limited.

In the above-described embodiment, the annular contact portion 43 is connected to the fixing member accommodation hole 35 by two connection portions 44, but they may be connected to each other at three or more positions.

In the above-described embodiment, the fixing member holding portion 42 has the annular contact portion 43 and the connection portion 44. However, the type is not particular limited when the fixing member 28 may be held inside the fixing member accommodation hole 35 and the holding of the fixing member 28 is released when the stopper body 29 is pulled.

In the above-described embodiment, an example has been described in which the fixing member 28 is divided into two pieces, but a fixing member which is divided into three or more pieces may be used.

In the above-described embodiment, the forceps stopper 21 which is attached to the ferrule 20 of the forceps opening 17 has been exemplified. However, the present invention may be applied to the forceps stopper which is directly attached to the opening portion 17a of the forceps opening 17.

In the above-described embodiment, the forceps stopper 21 which is attached to the ferrule 20 communicating with the forceps channel 16 has been exemplified. However, the present invention may be applied to, for example, a stopper which is attached to an opening portion communicating with a pipe line or various channels disposed inside the endoscope 10, such as a suction channel and an air and water supply channel.

In the above-described embodiments, the endoscope 10 which is inserted into a trachea has been exemplified. However, the present invention may be applied to, for example, an endoscope which is used in other industrial purposes or various medical endoscopes such as a large intestine endoscope which is inserted into a large intestine.

What is claimed is:

1. A stopper that is installed in an outer surface of an endoscope and is attached to a cylindrical opening portion communicating with a channel inside the endoscope, the stopper comprising:
a first fixing member having a first engagement portion engaging with an outer peripheral surface of the opening portion;

a second fixing member having a second engagement portion engaging with an outer peripheral surface of the opening portion; and a stopper body that has a retaining hole configured to retain the first fixing member and the second fixing member in said retaining hole and is attached to the opening portion through the first fixing member and the second fixing member;

wherein the first fixing member and the second fixing member retained in the retaining hole form an insertion hole allowing the opening portion to be inserted thereinto and the first engagement portion and the second engagement portion are formed in an inner wall continuous to the insertion hole;

the stopper further comprising a fixing member holding portion that is installed in the stopper body, wherein said fixing member holding portion holds the first fixing member and the second fixing member retained in the retaining hole, and is broken so as to release the first fixing member and the second fixing member from said retaining hole when the stopper body is pulled toward the front side of the opening portion.

2. The stopper according to claim 1,
wherein the engagement portion is an annular protrusion that is formed in an inner surface of the insertion hole along the circumferential direction of the insertion hole and is divided into a plurality of pieces along the circumferential direction, and
wherein the annular protrusion engages with a flange that is formed in the outer peripheral surface of the opening portion.

3. The stopper according to claim 2,
wherein the inner diameter of the annular protrusion is equal to or larger than the outer diameter of the opening portion and is smaller than the outer diameter of the flange.

4. The stopper according to claim 3,
wherein the fixing member holding portion has
an annular contact portion that is formed on an opening of the retaining hole and comes into contact with the annular protrusion, and
a connection portion that connects an opening peripheral edge portion of the retaining hole to the contact portion at a plurality of positions, and
wherein when the stopper body is pulled, the connection portion is broken.

5. The stopper according to claim 3,
wherein the stopper body is formed of an elastic material, and
wherein the retaining hole is deformed so as to increase in diameter in a manner such that the annular protrusion is widened in the radial direction by the flange until the annular protrusion comes into contact with the flange and rides over the flange when the opening portion is inserted into the insertion hole, and restores to an original shape when the annular protrusion rides over the flange.

6. The stopper according to claim 3,
wherein the annular protrusion has an inclined surface that is formed by cutting an opening peripheral edge portion on the opposite side of the forward direction.

7. The stopper according to claim 3,
wherein the fixing member is formed of a rigid material.

8. The stopper according to claim 3,
wherein the fixing member is divided into two pieces along the circumferential direction of the opening portion.

9. An endoscope comprising:
an operating portion that is connected to a base end portion of an insertion portion inserted into a subject;
a cylindrical opening portion that is formed in an outer peripheral surface of the operating portion and communicates with a channel inserted through the insertion portion; and
the stopper that is attached to the opening portion according to claim 3.

10. The stopper according to claim 2,
wherein the fixing member holding portion has
an annular contact portion that is formed on an opening of the retaining hole and comes into contact with the annular protrusion, and
a connection portion that connects an opening peripheral edge portion of the retaining hole to the contact portion at a plurality of positions, and
wherein when the stopper body is pulled, the connection portion is broken.

11. The stopper according to claim 2,
wherein the stopper body is formed of an elastic material, and
wherein the retaining hole is deformed so as to increase in diameter in a manner such that the annular protrusion is widened in the radial direction by the flange until the annular protrusion comes into contact with the flange and rides over the flange when the opening portion is inserted into the insertion hole, and restores to an original shape when the annular protrusion rides over the flange.

12. The stopper according to claim 2,
wherein the annular protrusion has an inclined surface that is formed by cutting an opening peripheral edge portion on the opposite side of a forward direction.

13. The stopper according to claim 2,
wherein the fixing member is formed of a rigid material.

14. The stopper according to claim 2,
wherein the fixing member is divided into two pieces along the circumferential direction of the opening portion.

15. An endoscope comprising:
an operating portion that is connected to a base end portion of an insertion portion inserted into a subject;
a cylindrical opening portion that is formed in an outer peripheral surface of the operating portion and communicates with a channel inserted through the insertion portion; and
the stopper that is attached to the opening portion according to claim 2.

16. The endoscope according to claim 15,
wherein the channel is a treatment tool channel through which a treatment tool is inserted.

17. The stopper according to claim 1,
wherein the fixing member is formed of a rigid material.

18. The stopper according to claim 1,
wherein the fixing member is divided into two pieces along the circumferential direction of the opening portion.

19. An endoscope comprising:
an operating portion that is connected to a base end portion of an insertion portion inserted into a subject;
a cylindrical opening portion that is formed in an outer peripheral surface of the operating portion and communicates with a channel inserted through the insertion portion; and
the stopper that is attached to the opening portion according to claim 1.

20. The endoscope according to claim 19,
wherein the channel is a treatment tool channel through which a treatment tool is inserted.

* * * * *